United States Patent [19]

Gore

[11] 4,239,578
[45] Dec. 16, 1980

[54] APPARATUS FOR INSERTING ELASTIC STRIPS DURING THE MANUFACTURE OF ELASTIC LEG DISPOSABLE DIAPERS

[75] Inventor: Graves T. Gore, Aiken, S.C.

[73] Assignee: Riegel Textile Corporation, Greenville, S.C.

[21] Appl. No.: 85,382

[22] Filed: Oct. 16, 1979

[51] Int. Cl.³ .......................................... B65H 25/00
[52] U.S. Cl. ............................... 156/361; 156/164; 156/229; 156/366; 156/495
[58] Field of Search ................................ 156/290–292, 156/183, 474, 160, 163–164, 229, 494, 495, 361, 351, 350, 366, 217; 128/284 R, 287, 291, 292; 2/402; 112/121.26, 414

[56] References Cited

U.S. PATENT DOCUMENTS

| Re. 28,139 | 8/1974 | Gore | 156/467 |
|---|---|---|---|
| 2,183,257 | 12/1939 | Hardie et al. | 112/414 |
| 3,488,778 | 1/1970 | Goujon | 2/402 |
| 3,560,292 | 2/1971 | Butter | 156/229 |
| 3,616,770 | 11/1971 | Blytheis et al. | 112/121.26 |
| 3,663,962 | 5/1972 | Burger | 2/402 |
| 3,828,367 | 8/1974 | Bourgeois | 186/217 X |
| 3,860,003 | 1/1975 | Buell | 128/287 |
| 3,964,410 | 6/1976 | Boser | 112/121.26 |
| 3,984,272 | 10/1976 | Teed | 156/201 |
| 4,024,824 | 5/1977 | Haff | 112/121.26 |
| 4,050,462 | 9/1977 | Woon et al. | 128/290 R |
| 4,081,301 | 3/1978 | Buell | 106/291 X |

*Primary Examiner*—David A. Simmons
*Attorney, Agent, or Firm*—Bell, Seltzer, Park & Gibson

[57] ABSTRACT

Apparatus for inserting elastic strips into elastic leg diapers in accordance with the improved elastic leg disposable diaper and process for manufacturing same disclosed in co-pending U.S. patent application Ser. No. 85,372, filed concurrently herewith, and assigned to the assignee of the present invention, wherein elastic strips are adhesively secured continuously along the longitudinal edges of the disposable diaper and are alternately secured in stretched condition along the crotch area and in relaxed condition along the outer waist areas to form gathered and extendible side portions in the crotch area for elastic compliance to the legs of the wearer including mechanisms for alternately stretching and relaxing predetermined lengths of the continuous elastic strips.

5 Claims, 5 Drawing Figures

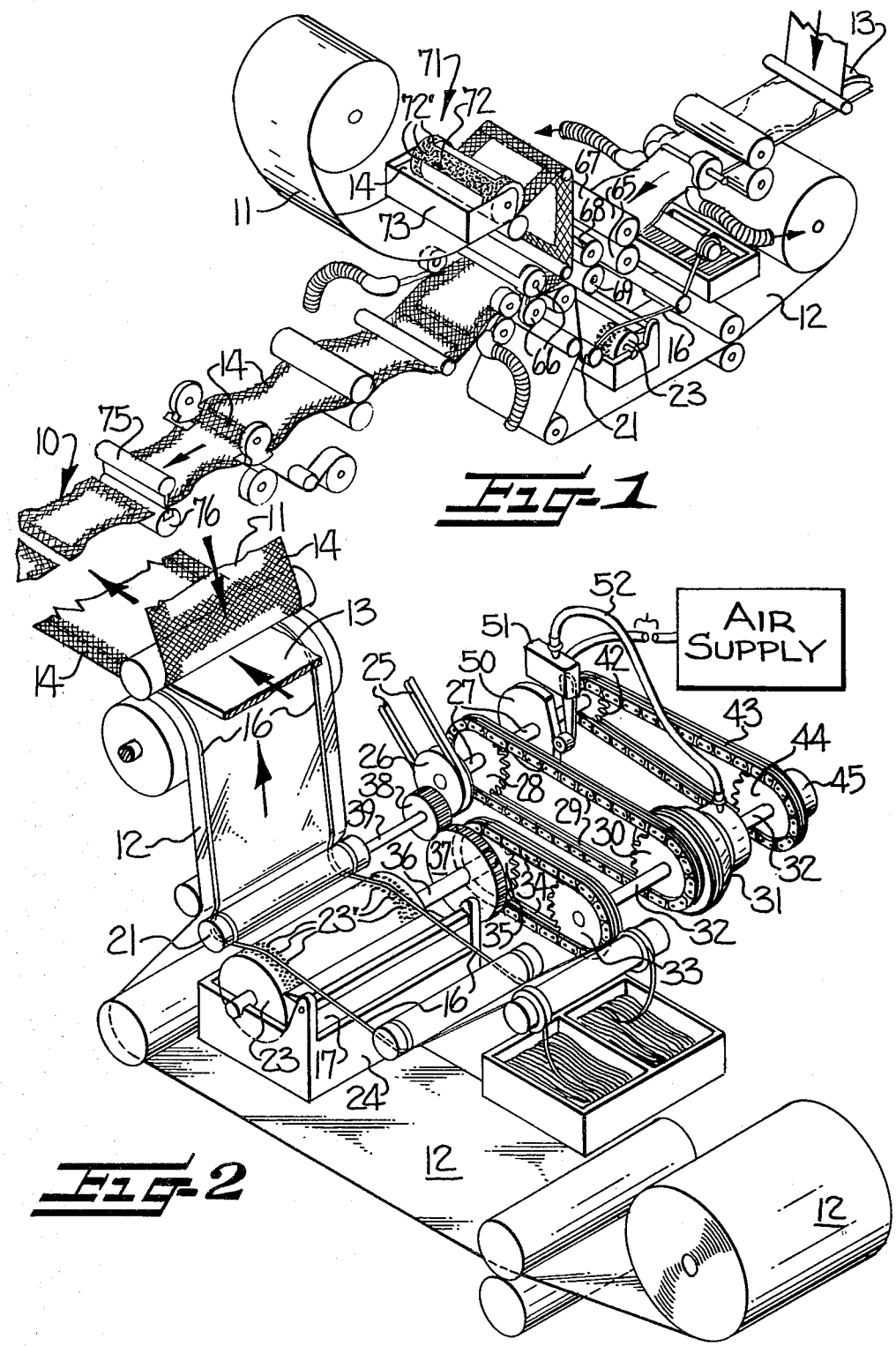

APPARATUS FOR INSERTING ELASTIC STRIPS DURING THE MANUFACTURE OF ELASTIC LEG DISPOSABLE DIAPERS

FIELD OF THE INVENTION

This invention relates to an apparatus for inserting elastic strips into elastic leg diapers in accordance with the improved elastic leg disposable diaper and process for manufacturing same disclosed in co-pending U.S. patent application Ser. No. 085,372, filed concurrently herewith, and assigned to the assignee of the present invention, wherein elastic strips are adhesively secured continuously along the longitudinal edges of the disposable diaper and are alternately secured in stretched condition along the crotch area and in relaxed condition along the outer waist areas to form gathered and extendible side portions in the crotch area for elastic conformance with the legs of the wearer.

BACKGROUND OF THE INVENTION

The improved elastic leg diaper product and process for inserting elastic strips therein which are alternatively stretched and relaxed and continuously secured along the longitudinal edges of the diaper to overcome the problems resulting from prior art processes to produce an improved diaper product are fully set forth in assignee's above identified copending application and reference may be had thereto for a full discussion of same.

It is the object of this invention to provide an apparatus for attaching elastic strips in elastic leg disposable diapers having gathered and extensible side portions in the crotch area during the manufacture of such diapers in an assembly machine in accordance with the process and resulting elastic leg disposable diaper product of assignee's above discussed copending application.

SUMMARY OF THE INVENTION

By this invention, it has been found that the above object may be accomplished by providing such apparatus including means for alternately stretching and relaxing predetermined lengths of the continuous elastic strips comprising generally the following.

Selectively variable drive means are connected with the elastic strip feeding means and are selectively operable for driving the feeding means for alternately feeding of the elastic strips at a first speed substantially equal to the speed of movement of the serially-interconnected diapers in the assembly machine for maintaining the elastic strips in relaxed condition and at a second speed less than the speed of movement of the serially-interconnected diapers in the assembly machine for stretching the elastic strips. Control means are operatively connected with the drive means for alternately actuating the drive means for the first and second speeds of feed of the elastic strips for alternately stretching and relaxing predetermined lengths of the elastic strips.

BRIEF DESCRIPTION OF THE DRAWINGS

Some of the objects and advantages of this invention having been set forth, other objects and advantages will appear when taken in conjunction with the accompanying drawings, in which:

FIG. 1 is a schematic perspective view of apparatus in accordance with this invention;

FIG. 2 is an enlarge schematic perspective view, taken from a different angle, of a portion of the apparatus of FIG. 1 and further illustrating the details of the apparatus of this invention;

DETAILED DESCRIPTION OF THE INVENTION

Figure 3:
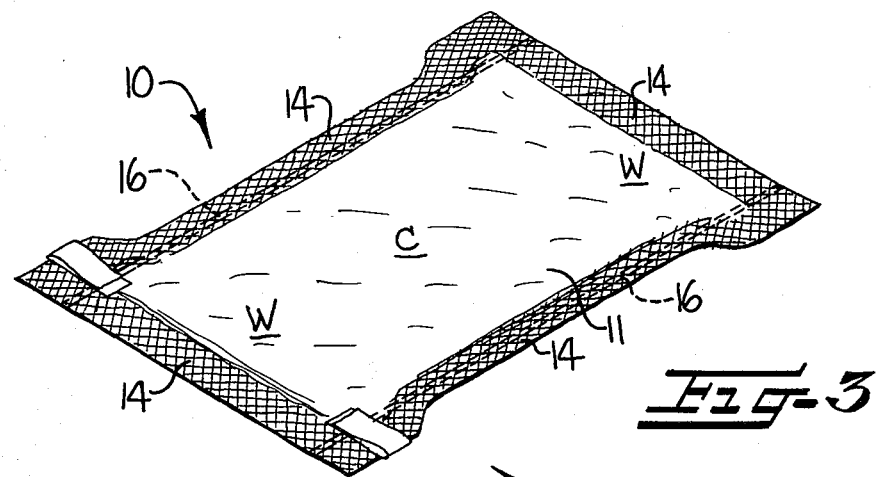
FIG. 3 is a top perspective view of an elastic leg diaper produced by the apparatus of this invention and shown in the stretched extended condition.
Figure 4:
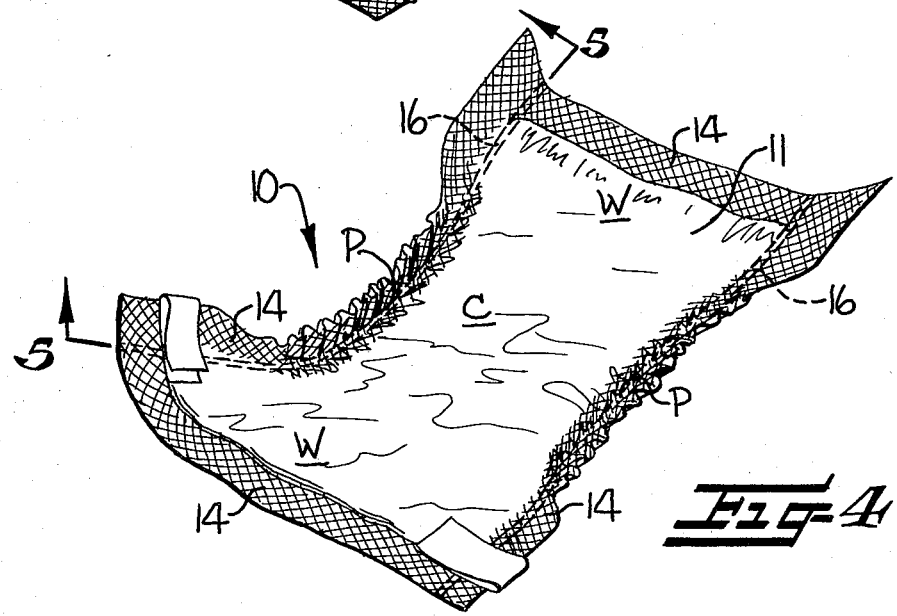
FIG. 4 is a top perspective view of the diaper of FIG. 3 shown in the relaxed condition.
Figure 5:
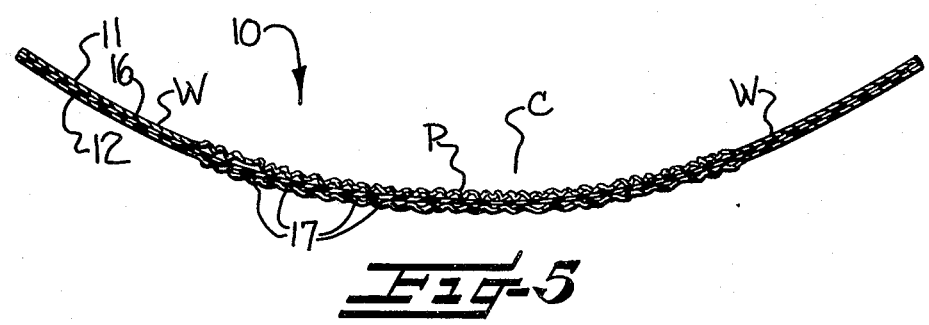
FIG. 5 is a cross sectional view taken through the elastic strips along the longitudinal edge of the diaper and generally along the line 5—5 of FIG. 4.

In the drawings, FIGS. 1 and 2 illustrate the apparatus for inserting elastic strips during the manufacture of elastic leg disposable diapers in accordance with this invention and FIGS. 3–5 illustrate the resulting elastic leg disposable diaper product.

Referring firstly to the product produced by the apparatus of this invention for purposes of background, the improved elastic leg disposable diaper, as discussed more fully in the above-discussed copending application of the assignee of this invention, is generally referred to by the reference numeral 10. The diaper 10 is preferably of generally hour-glass configuration and has a central crotch-fitting area C and outer waist-fitting areas W designed to be placed around the crotch and waist of the wearer when the diaper 10 is placed on the wearer in conventional manner. The diaper 10 further includes a fluid-permeable top cover sheet 11, a fluid-impermeable bottom cover sheet 12 and fluid-absorbent interior pad 13, all of which may be of conventional construction.

The disposable diaper 10 is secured along its longitudinal and transverse edges by suitable adhesive or other attachment means 14 which secures the top sheet 11 to the bottom sheet 12 and generally provides an envelope around the interior pad 13 which is unsecured at its longitudinal edges and in the central crotch area C to either the top cover sheet or bottom cover sheet to allow the pad to conform to the shape of the diaper when placed in position on the wearer.

The diaper 10 further includes elastic strips 16 extended and being secured by adhesive or other suitable means 17 (see FIG. 5) to the diaper 10 continuously along the full length of the outside longitudinal edges of the diaper 10. Elastic strips are secured in the crotch area C in stretched elastically-contractible condition forming gathered and extendible side portions P in the crotch area C (see FIGS. 4 and 5) for elastic conformance with the legs of the wearer and are secured in the waist areas W in less elastically-contractible or relaxed condition so as to provide less or no gathering of the side portions of the waist areas W.

Referring now to the apparatus of the present invention, FIGS. 1 and 2 illustrate schematically an apparatus for manufacturing elastic leg disposable diapers 10 utilizing the apparatus of this invention for inserting the elastic strips 16 during the manufacture of such elastic leg disposable diapers 10. The apparatus of this invention is shown schematically therein and many of the drives of the overall diaper manufacturing apparatus are eliminated for purposes of clarity of the disclosure and such drives or other devices may be easily designed by those with ordinary skill in the art. However, details of construction and operation of apparatus for manufacturing disposable diapers may be seen in co-pending application Serial No. 046,114, filed June 6, 1979 and prior U.S. Patents Re. 28,139 and 3,984,272, all of which are assigned to the assignee of the present invention and which are applicable for use with the apparatus for inserting elastic strips of the present invention.

Referring now to FIG. 1 and the apparatus for manufacturing disposable diapers, connected mutlilayer absorbent pads 13 are fed through pairs of driven feed rolls 65, 66 between which is provided a pad severing means in the form of a rotating cutting roll 67 having a knife blade 68 thereon and an anvil roll 69 which operate to intermittently cut the interconnected multi-layer pads 13 transversely for separation of the interconnected pads 13. The driven feed rolls 66 are driven somewhat faster than the driven feed rolls 65 to effect an overfeeding of the severed multi-layer absorbent pads 13 for spacing the pads apart in the further fabrication of the disposable diapers 10.

Immediately prior to the feed rolls 66, the top cover sheet 11 is fed from a suitable source of supply to feed rolls 66 and through a glue applicator 71 which applies the glue or adhesive 14 of a suitable type in a predetermined pattern across the cover sheet 11 at spaced locations and along the longitudinal edges of the top cover sheet 11 for purposes of gluing the transverse and longitudinal edges of the ultimately fabricated disposable diaper 10 together. Glue applicator 71 may comprise any suitable glue applicator for the above purpose and as illustrated herein may include a glue applicator roll 72 having indentations or cups 72' therein which collectively are of the predetermined configuration of the areas for receiving adhesive 14. The applicator roll 72 may pass through an adhesive supply tank 73 for containing a supply of the adhesive 14.

Simultaneously with the above, the bottom cover sheet 12 is fed from a source of supply to feed rolls 66 and into superimposed position under the spaced-apart interior pads 13 and top cover sheet 11 so that all of these components are in superimposed position. The top cover sheet 11 and bottom cover sheet 12 are pressed into contact with each other by the feed rolls 66 and subsequent rolls and are adhesively secured together along longitudinal edges and transversely between the separated and spaced-apart absorbent pads to form serially-interconnected disposable diapers 10 which are continuously fed through the remaining portions of the apparatus by suitable feeding means.

These serially-interconnected diapers 10 are fed through a series of mechanisms, not shown, and are ultimately fed between cutter roll 75 and anvil roll 76 which cut the serially-interconnected diapers 10 transversely between interior pads to form individual diapers 10.

Cooperating with the above-described apparatus for manufacturing disposable diapers 10, apparatus in accordance with this invention is provided for inserting the elastic strips 16 during the manufacture of such disposable diapers 10. This apparatus is more specifically illustrated in FIG. 2 and includes means for feeding continuous elastic strips 16 with adhesive thereon along the entire length thereof into desired position for adhesive attachment in the diapers. As illustrated in FIG. 2, the feeding means may include driven feed roll 21 mounted to receive elastic strips 16 from a suitable source of supply and feed the continuous elastic strips into engagement with the bottom cover sheet 12 and into engagement between guide rolls of the apparatus assembling the disposable diapers and receiving the top cover sheet 11, bottom cover sheet 12 and interior pads in superimposed position.

In the case of the apparatus illustrated herein, the elastic strips 16 are fed into contact with and over an adhesive applicator roll 23 which includes cups or indentations 23' therein for picking up adhesive 17 as it passes through a supply tank 24 containing such adhesive 17. The applicator roll 23 is adapted to apply adhesive continuously along the entire face of the elastic strips 16 as they are fed by feed roll 21. The adhesive 17 is desirably of a fast-acting type since the elastic strips are being secured in both the stretched and relaxed conditions and the adhesive must set up as soon as the elastic strips are moved into contact with one of the components of the disposable diaper 10, such as the bottom cover sheet 12 in the case of the apparatus illustrated in FIG. 2.

For driving the feed roll 21 to effect alternate stretching and relaxing of the elastic strips 16, selectively variable drive means are provided.

As illustrated in FIG. 2, this selectively variable drive means may include a first selectively operable drive means comprising a belt 25 driven from a suitable motor or other drive mechanism which passes around pulley 26 to rotate shaft 27 which carries sprocket gear 28 thereon. Sprocket gear 28 receives chain 29 which in turn drives sprocket 30 which is connected through a pneumatic clutch 31 to shaft 32 which drives sprocket 33, chain 34 and sprocket 35. Sprocket 35 in turn drives shaft 36 which is connected to and rotates glue applicator roll 23. The shaft 36 carries gear 37 which meshes with gear 38 carried on the drive shaft 39 of feed roll 21 for driving of feed roll 21.

The above-described drive constitutes a first drive means for the elastic strip feeding means, i.e. feed roll 21, and is constructed when actuated through pneumatic clutch 31 to feed the elastic strips 16 at substantially the same speed of travel as the components 11, 12, 13 of the disposable diapers are traveling through the disposable diaper manufacturing apparatus, described above, so that the elastic strips 16 will be secured within the disposable diapers 10 in relaxed condition.

A second selectively operable drive means is provided which includes sprocket 42 carried on shaft 27 and driving chain 43 which in turn drives sprocket 44 which drives shaft 32 through slip clutch 45 and thus drives adhesive applicator roll 23 and feed roll 21 through the above-described drive mechanisms. This last described second drive means is a slower speed drive means and when operable will drive the feed roll 21 at a speed less than the speed of travel of the components 11, 12, 13 of the disposable diapers through the disposable diaper manufacturing apparatus, so that the elastic strips 16 will be stretched since the feed roll 21 is in effect underfeeding the elastic strips 16 into engagement with the diapers 10. As illustrated in FIG. 2, this stretch will occur between the roll 21 and the point in which the elastic strips 16 are brought into adhesive securing engagement with the bottom cover sheet 12.

For controlling operation of the above-described selectively operable first and second drive means, there is provided a timed control means which is operatively connected with each of the drive means for alternately actuating each of the drive means in correlation with the speed of movement of the diapers 10 through the assembly machine and the lengths of the longitudinal edges of the crotch area C and the waist areas W to which alternate lengths of stretched and relaxed portions of the elastic tapes 16 are to be secured.

This timed control means may comprise a cam 50 mounted on and rotated by drive shaft 27 and which includes a cut-out portion and a lobe portion thereon designed to open and close valve 51 contained within an air conduit 52 extending from any suitable source of air supply to the pneumatic clutch 31, so that, when the valve 51 is opened by the cam 50, the air clutch 31 will be actuated to effect operation of the first drive means which drives the feed roll 21 at a faster speed of travel. When the cam 50 closes valve 51 and thus deactuates pneumatic clutch 31, the feed roll 21 will be driven through the second drive means through the slip clutch 45. It will be understood by those with ordinary skill in the art that the slip clutch 45 will slip when the faster drive through pneumatic clutch 31 is operating.

The cam 50 may be easily designed by one with ordinary skill in the art to open and close valve 51 in accordance with the lengths of the longitudinal edges of the respective crotch area and waist areas of the serially-interconnected diapers 10 so that the alternately stretched and relaxed lengths of the elastic strips 16 may be applied in desired position within the diapers 10.

Thus, this invention has provided an apparatus for inserting elastic strips 16 into elastic leg diapers 10 in accordance with the improved elastic leg diaper and process for manufacturing same disclosed in assignee's above-discussed co-pending U.S. patent application and which includes means for alternately stretching and relaxing predetermined lengths of the continuous elastic strips 16 during the feeding thereof for attaching the stretched lengths to the crotch area C and the substantially relaxed lengths to the outer waist areas W continuously along the longitudinal edges of the elastic leg diapers 10 during manufacture of such diapers in an assembly machine.

In the drawings and specification, there has been set forth a preferred embodiment of the invention and although specific terms are employed, they are used in a generic and descriptive sense only and not for purposes of limitation.

What is claimed is:

1. In an apparatus for attaching elastic strips in elastic leg disposable diapers having gathered and extendible side portions in the crotch area during the manufacture of such diapers in moving serially-interconnected form in an assembly machine and including means for feeding continuous elastic strips into desired position in the diaper for adhesive attachment therein and means for alternately stretching and relaxing predetermined lengths of the elastic strips during the feeding thereof for attaching the stretched lengths to the crotch area and the substantially relaxed lengths to the outer waist areas continuously along the longitudinal edges of the diapers; the improvement of said means for alternately stretching and relaxing predetermined lengths of the continuous elastic strips comprising: selectively variable drive means connected with said elastic strip feeding means for driving said feeding means at a first speed substantially equal to the speed of movement of the serially-interconnected diapers in the assembly machine for maintaining the elastic strips in relaxed condition and at a second speed less than the speed of movement of the serially-interconnected diapers in the assembly machine for stretching the elastic strips; and control means operatively connected with said drive means for alternately actuating said drive means for the first and second speeds of feed of the elastic strips for alternately stretching and relaxing predetermined lengths of the elastic strips.

2. In an apparatus, as set forth in claim 1, in which said selectively variable drive means comprises first drive means connected with said elastic strip feeding means and said control means for being selectively operated for driving said elastic strip feeding means the first speed, and second drive means operatively connected with said elastic strip feeding means and said control means for being selectively operated for driving said elastic strip feeding means at the second speed.

3. In an apparatus, as set forth in claim 2, in which said control means includes timing means for alternately operating said first and second drive means in correlation with the speed of movement of the diapers through the assembly machine and the lengths of the longitudinal edges of the crotch area and the waist areas to which alternate lengths of stretched and relaxed portions of the elastic tapes are to be adhered.

4. In an apparatus for attaching elastic strips in elastic leg disposable diapers having gathered and extendible side portions in the crotch area during manufacture of such diapers in moving serially-interconnected form in an assembly machine and including means for feeding continuous elastic strips having adhesive thereon along the entire length thereof into desired position in the diaper for adhesive attachment therein and means for alternately stretching and relaxing predetermined lengths of the elastic strips during the feeding thereof for attaching the stretched lengths to the crotch area and the substantially relaxed lengths to outer waist areas continuously along the longitudinal edges of the diapers; the improvement of said means for alternately stretching and relaxing predetermined lengths of the continuous elastic strips comprising: driven feed roll means cooperating with and forming a part of said elastic strip feeding means; first drive means connected with and selectively operable for driving said feed roll means at a first predetermined speed for feeding of the elastic strips at a speed substantially equal to the speed of movement of the serially-interconnected diapers in the assembly machine for maintaining the elastic strps in relaxed condition; second drive means connected with and selectively operable for driving said feed roll means at a second predetermined speed less than the speed of movement of the serially-interconnected diapers in the assembly machine for stretching the elastic strips; and timed control means operatively connected with said first and second drive means for alternately actuating said first and second drive means in correlation with the speed of movement of the diapers through the assembly machine and the lengths of the longitudinal edges of the crotch area and the waist areas to which alternate lengths of stretched and relaxed portions of the elastic tapes are to be secured.

5. Apparatus for manufacturing elastic leg disposable diapers having a central crotch-fitting area, outer waist-fitting areas and elastic extendible side portions in the crotch area, said apparatus including: feeding means for superimposing a continuous fluid-permeable top cover sheet, a continuous fluid-impermeable bottom cover sheet and spaced-apart fluid-absorbent interior pads between the top and bottom cover sheets while feeding such components through said apparatus; means for securing the top cover sheet and the bottom cover sheet together along longitudinal edges and transversely between the individual pads to form serially-interconnected disposable diapers; means for attaching elastic strips continuously along the entire length of the longitudinal edges of each of the diapers including means for feeding continuous elastic strips having adhesive along the entire length thereof into desired position for adhesive attachment in the diapers and means for alternately stretching and relaxing predetermined lengths of the elastic strips during the feeding thereof for attaching the stretched lengths to the crotch area and the substantially relaxed lengths to the outer waist areas of the diapers comprising selectively variable drive means connected with said elastic strip feeding means and being selectively operable for driving said feeding means for alternately feeding of the elastic strips at a first speed substantially equal to the speed of movement of the serially-interconnected diapers through said apparatus for maintaining the elastic strips in relaxed condition and at a second speed less than the speed of movement of the serially-interconnected diapers through said apparatus for stretching and elastic strips, and control means operatively connected with said drive means for alternately actuating said drive means for the first and second speeds of feed of the elastic strips for alternately stretching and relaxing predetermined lengths of the elastic strips; means for cutting the interconnected diapers individually between the interior pads to form individual diapers; whereby, the stretched lengths of the elastic strips are contracted and form gathered and extendible side portions in the crotch areas of the individual diapers.

* * * * *

UNITED STATES PATENT AND TRADEMARK OFFICE
CERTIFICATE OF CORRECTION

PATENT NO. : 4,239,578

DATED : December 16, 1980

INVENTOR(S) : Graves T. Gore

It is certified that error appears in the above–identified patent and that said Letters Patent are hereby corrected as shown below:

Column 4, line 58, after "the" (first occurrence) insert --feed--; Column 8, line 4, after "stretching" delete "and" and insert --the--.

Signed and Sealed this

Seventeenth Day of July 1984

[SEAL]

Attest:

Attesting Officer

GERALD J. MOSSINGHOFF

Commissioner of Patents and Trademarks